United States Patent [19]

Ehrlich et al.

[11] Patent Number: 4,783,751
[45] Date of Patent: Nov. 8, 1988

[54] ANALYSIS OF PORE COMPLEXES

[75] Inventors: Robert Ehrlich; Sterling J. Crabtree, Jr.; Robert Cannon, all of Columbia, S.C.

[73] Assignee: University of South Carolina, Columbia, S.C.

[21] Appl. No.: 16,495

[22] Filed: Feb. 17, 1987

Related U.S. Application Data

[63] Continuation of Ser. No. 524,022, Aug. 17, 1983, abandoned.

[51] Int. Cl.⁴ ............... G06F 15/62; G06F 15/70; G01N 33/24
[52] U.S. Cl. ................... 364/506; 250/311; 356/380; 364/518
[58] Field of Search ............... 364/416, 498, 506, 518, 364/519, 521; 250/307, 310, 311; 356/203, 378, 379, 380, 381, 402

[56] References Cited

U.S. PATENT DOCUMENTS

| | | | |
|---|---|---|---|
| 3,449,586 | 6/1969 | Serra | 250/559 |
| 3,805,035 | 4/1974 | Serra | 382/28 |
| 3,940,737 | 2/1976 | Beun | 382/49 |
| 3,999,047 | 12/1976 | Green | 364/416 X |
| 4,125,828 | 11/1978 | Resnick et al. | 364/416 X |
| 4,146,788 | 3/1979 | Mirkin et al. | 250/311 |
| 4,191,940 | 3/1980 | Polcyn et al. | 364/416 X |
| 4,197,012 | 4/1980 | Kerenyi et al. | 356/380 |
| 4,249,827 | 2/1981 | Di Matteo et al. | 356/402 |
| 4,328,426 | 5/1982 | D'Ortenzio | 364/724 |
| 4,350,998 | 9/1982 | Verhoeven | 364/724 X |
| 4,406,545 | 9/1983 | Montone et al. | 356/380 |
| 4,439,680 | 3/1984 | Broadhurst | 250/310 |
| 4,491,926 | 1/1985 | Okada et al. | 364/416 |
| 4,503,555 | 3/1985 | Brimhall, Jr. et al. | 364/518 X |

FOREIGN PATENT DOCUMENTS 0053263 6/1982 European Pat. Off. .
1576971 12/1977 United Kingdom .

OTHER PUBLICATIONS

Angewandte Informatik, vol. 21, No. 11, Nov. 1979, (Wiesbaden, DE), P. Zamperoni: "Erosion und Dilatation als umkehrbare Operationen zur Musteranalyse", pp. 487–494.
(Radio Mentor Electronic, vol. 40, No. 3, 1974 (Munchen, DE).
G. Kamin: "Der Geometrie-Computer", pp. 105–108.
Proceedings of the Fourth International Joint Conference on Pattern Recognition, Nov. 7–10, 1978, Kyoto, JP; IEEE 1979 (New York U.S.) M. Onoe: "Recognition of Adenocarcinoma in Automated Uterine Cytology", pp. 883–885.

(List continued on next page.)

Primary Examiner—Felix D. Gruber
Attorney, Agent, or Firm—Brunbaugh, Graves, Donohue & Raymond

[57] ABSTRACT

Analog signals corresponding to color images or pixels of a thin section of a rock reservoir are digitized and then filtered to isolate the pixels representative of pores in the thin section. The pores so isolated are then counted, measured for their total pore perimeter and labelled.

Each area of pixels representative of pores of value one is progressively eroded and dilated, pursuant to which one layer of pixels of ones on the perimeter of the area is converted to zeros and, if a seed pixel remains, one layer of pixels of ones is added to the perimeter of the area. Thereafter, the original object undergoes two successive erosions followed by two dilations if a seed pixel remains. Successive iterations of the erosion and dilation cycle continue until the last erosion eliminates the seed pixel of the area. The numbewr of pixels of ones lost with each degree of erosion constitutes a pore spectrum consisting of information relating to the total amount of pore image lost each erosion-dilation cycle, the pore size lost each erosion-dilation cycle and the pore roughness lost each cycle.

The spectra devleoped from the erosion-dilation cycle and corresponding to each pore complex are then analyzed into end members and the end member proportions for each field of view are calculated.

14 Claims, 10 Drawing Sheets

OTHER PUBLICATIONS

Article entitled "Characterization of Pore Structure by a Combination of Quantitative Photomicrography and Mercury Porosimetry" by F. A. L. Dullien and G. K. Dhawan; Journal of Colloid and INterface Science, vol. 47, No. 2, May 1974, pp. 337–349.

Article entitled "A Computerized Quantitative Image Analysis Procedure for Investigating Features and an Adapted Image Process" by Manfred Rink; Journal of Microscopy, vol. 107, Pt. 3, Aug. 1976, pp. 267–286;

Article entitled "Pore Structure and Physical Properties of Porous Sedimentary Rocks" by M. Rink and J. R. Schopper; Pageoph, vol. 114 (1976), Virkhauser Verlag, Basel.

Computer Graphics and Image Processing, vol. 17, 1981 (US) I. T. Young et al.: "A New Implantation for the Binary and Minkowski Operators", pp. 189ƒ210.

ANALYSIS OF PORE COMPLEXES

This application is a continuation of application Ser. No. 524,022, filed on 8/17/83, now abandoned.

BACKGROUND OF THE INVENTION

In sedimentary petrography, small-scale samples of reservoir rocks, such as the sections, peels, and slabs, are typically analyzed and studied. An early objective of the study of such samples was the deduction of the characteristics of the sediment shortly after deposition.

Carbonates recrystallize much more readily and pervasively than detrital sandstones. As a result, an awareness of an accessible record of post depositional history came earlier to carbonate petrologists than to sandstone petrologists. Interest in diagenetic state and history increased as it became clear that much porosity in petroleum reservoirs, both carbonate and detrital, is secondary and also that diagenetic mineral phases growing on pore walls could adversely affect hydrocarbon recovery. Intensive research on reservoir quality using thin section and scanning electron microscope (SEM) imagery, together with complementary geochemical-/isotropic data, has moved this part of the study of diagenesis from an area of speculation to the presently applied science of reservoir assessment.

Petrologists have come to treat pores as compositional phases. This has more than pragmatic justification. Pores are not mere voids, but signify the occurrence of a fluid or gaseous phase. A pore/pore wall interface possesses surface energy exactly in the same way as a quartz/feldspar interface; growth or loss of pores can be thought to operate under the dynamic/kinetic parameters which affect the stability of the surrounding solid phases. Indeed, in order to define a general measure of the extent and direction of diagenesis of a rock unit, measurements of pore characteristics can serve as a first order diagenetic variable.

Permeability in reservoir rocks occurs through a three-dimensional interconnected pore network. Conventionally, the wider parts of the network are termed "pores" and the narrower parts are termed "pore throats". The three-dimensionality of the pore complex has been directly observed by dissolving the rock matrix to leave an epoxy-impregnated framework.

Most observations of pores are from thin sections or SEM imagery which provide limited direct three-dimensional information. In reservoir studies, it is important that three-dimensional information concerning the pore complex be developed for an understanding of fluid flow and its correlation with petrophysical data such as capillary pressure curves and wire line log response. What is desired is a quantitative variable or variables derived from the two-dimensional pore complex which can then be correlated with petrophysical and geophysical measurements as well as with the response of the reservoir to production.

It is assumed that the pore system displayed on an essentially two-dimensional slice bears some relationship to the three-dimensional network from which it was extracted. Direct extrapolation from two-dimensional observations to the third dimension has not been achieved and may never be achieved without simplifying assumptions, e.g., spherical, hexagonally packed, grains. There is little doubt, however, that there must be some relationship, termed a "transfer function", between the pore complex intersected by a plane and the three-dimensional network. It is thus an assumption of the present application that significant changes in the three-dimensional network are reflected in changes in the two-dimensional section.

Sedimentary petrography represents a discipline which concerns analysis of micro-scaled imagery of sedimentary rocks. The data necessary to characterize pore-complex geometry in a single field of view generally is most expeditiously developed through computer-assisted analysis of the images. The general field of image analysis is relatively mature so that general principles and strategies have already been defined. That such an approach is required for pore complex analysis has been realized for more than a decade.

Image analysis requires an image acquisition system consisting of (1) a sensor such as a videoscanner, (2) an analog/digital converter to convert the analog television signal to digital form, and (3) a data processor. In the data processor, the digital representation of the scene is electronically arranged into an array of grid points or pixels. Each pixel is defined by three values: two spatial coordinates (X, Y) and a "gray level" intensity value. The gray level, a measure of brightness, is restricted to integral values. Because the pixels form a grid, once the grid spacing is known, the coordinates of each pixel are known implicitly by knowing the location of one pixel in the array. In the system of the present invention, three scenes of the same field of view are digitized through red, green and blue filters respectively. These three "color planes" when combined will produce a complete color image.

One of the main objectives in image analysis is image segmentation. Segmentation is the determination of which pixels in the array belong to the same category. For instance, an algorithm which subdivides a thin section image into the categories "quartz" and "others" necessarily accomplishes a segmentation with respect to quartz.

In the segmentation of pores, advantage is taken of the fact that piror to sectioning, the rocks can be impregnated with pigmented, typically, blue, epoxy. Because few, if any, constituents in reservoir rocks are naturally colored blue, segmentation can be achieved through a digital filter. A filter may consist of the average ratio of gray-level intensities from each color plane of red to green to blue of pixels located in pores. An image processing algorithm then compares that ratio with that of every pixel, and assigns, for example, a value of "one" to those with the "correct" ratio for pores and a "zero" for all others. The result is a binary image which ensures that in the subsequent analysis of pore geometry only the pores will be analyzed.

With the pore-complex identified, analysis of porosity can commence. Porosity is the proportion of pore pixels to total pixels in the scene. The porosity value estimated in this way is not the same as porosity as measured by physical tests. Pores are measured by the presence of blue-dyed epoxy impregnation. Thus, the porosity defined by petrographic image analysis is more closely linked to effective or interconnected porosity than to total porosity.

Most minerals in sedimentary rocks are transparent to translucent and this characteristic can in some cases affect porosity estimates. As the illumination level increases, more and more blue-dyed pores can be seen through mineral grains. Thus, increasing proportions of pores inclined or even parallel to the plane of section will be detected. The problem can be minimized by careful control of illumination and adjustment of the values of the digital filter.

Total pore perimeter is another property that is evaluated. This is an especially useful variable in that it has been shown that total pore perimeter per unit area is directly proportional to pore surface area per unit volume. The ratio of total pore area to the total pore perimeter can provide information concerning pore roughness or tortuosity.

Another variable tied to roughness/tortuosity is bending energy. It has been pointed out that perimeter measured from pixel to pixel along a periphery may deviate significantly from perimeter measured continuously. Bending energy, representing the energy necessary to deform a circle into the shape of the pore, is defined as the normalized sum of squares of curvature of the vertices of the periphery.

Bending energy can be calculated on a pore-by-pore basis. When summed or averaged, the pore measurements can be a global measure. Considering the fact that pores have quite complex geometries, bending energy is in fact a more generally useful variable than simpler measures of geometry such as measurements of long and intermediate axes. However, pores of many shapes can yield equivalent values of bending energy. What is needed in many cases is a way to measure subfeatures of a pore. It has been recognized that often pores can possess extended complex geometries and so conventional shape measurement variables would often be of little value. One prior art solution was to develop an algorithm that would subdivide the pore imagery into subdivisions of relatively simple geometry—each of which would then be efficiently evaluated by conventional shape and size variables.

SUMMARY OF THE INVENTION

It is accordingly an object of the present invention to provide a system for analyzing reservoir rock samples to produce data representative of the geometry of the pore complexes therein.

It is another object of the present invention to provide a system for analyzing reservoir rock samples to produce data representative of the number, size and type pores which exist in the reservoir rock.

These and other objects of the present invention are accomplished by developing digitized color images in the form of a grid of pixels of binary values of a thin section of a rock reservoir and then filtering such signals to isolate areas of pixels representative of pores in the thin section. The areas so isolated are then counted, measured for their total pore perimeter and labeled by a computer.

Each area of pixels representative of pores is then progressively eroded and dilated, pursuant to which the outer layer of pixels of each such area on the surface is eroded (converted to complementary value) and, if a seed pixel remains, an outer layer of pixels of the type characteristic of pores is added. Thereafter, the original object undergoes two successive erosions followed by two dilations if a seed pixel remains. Successive iterations of the erosion and dilation cycle continue until the last erosion eliminates from the area each pixel of the type representative of pores. The number of pixels converted with each degree of erosion constitutes a pore spectrum consisting of information relating to the total amount of pore image converted by each erosion-dilation cycle, the pore size converted by each erosion-dilation cycle and the pore roughness converted by each cycle.

The spectra developed from the erosion-dilation cycle and corresponding to each pore complex are then analyzed into end members and the end member proportions for each field of view are calculated.

DETAILED DESCRIPTION OF THE PREFERRED EMBODIMENT

Images of a thin section of reservoir rock are developed by digitizing an analog signal representing an electronic image of the thin section. As shown by the block 10 in FIG. 1A, a scanning microscope develops an analog signal representing a time varying voltage which is proportional to scene brightness. The analog signal is then supplied to an analog-to-digital converter 12 which converts the analog signal into a digital signal. As a part of the converter 12, the resulting digital signals are also sampled periodically to develop a grid of points or pixels.

One pass is sufficient for a black and white image, as produced by the scanning microscope. For the color scenes of the optical microscope, each field of view is digitized three times, once each through red, green and blue filters for each scene.

Generally, at least four fields of view are analyzed per thin section to measure small-scale spatial variability. Magnifications are chosen with respect to reservoir character and the problem to be solved. Pores at least as small as 0.3 microns can be detected.

Image segmentation is the process which identifies those pixels which belong to particular categories. Preferably, the pores in each thin section are filled with blue-dyed epoxy. Thus, a digital filter 14 consisting of the ratio and differences of red, green and blue intensities is sufficient to segment pores from non pores. Other more complex digital filters can distinguish clay from pore even if the clay is blue tinged. Carbonates are commonly stained and the spectral character of the stain is sufficient to distinguish carbonate types. Finally, gray-level segmentation can be used to distinguish carbonate textural types or detrital minerals.

Once pores are distinguished from the rock matrix, a binary image is developed wherein all pixels representing pores are set to black or a unit binary value and all other pixels are set to white or zero binary value. At this point the pore complex is in a form suitable for analysis. The analysis is then performed in a suitable processor 15 whose operation is shown in more detail in the flow chart of FIG. 1B. Basically the operation involves pore complex analysis as represented by block 16 erode-dilation iterations as represented by block 18, and finally classification of the data derived and stored into the desired complex pore spectra. Referring to FIG. 2, the first step in analysis is to assign a unique identification number to each pore in the image. Subsequent pore analysis operates on this catalogued set.

Analysis of the pore complex is accomplished at the processor 15 through a succession of operations each more progressively complex.

Figure 1A:
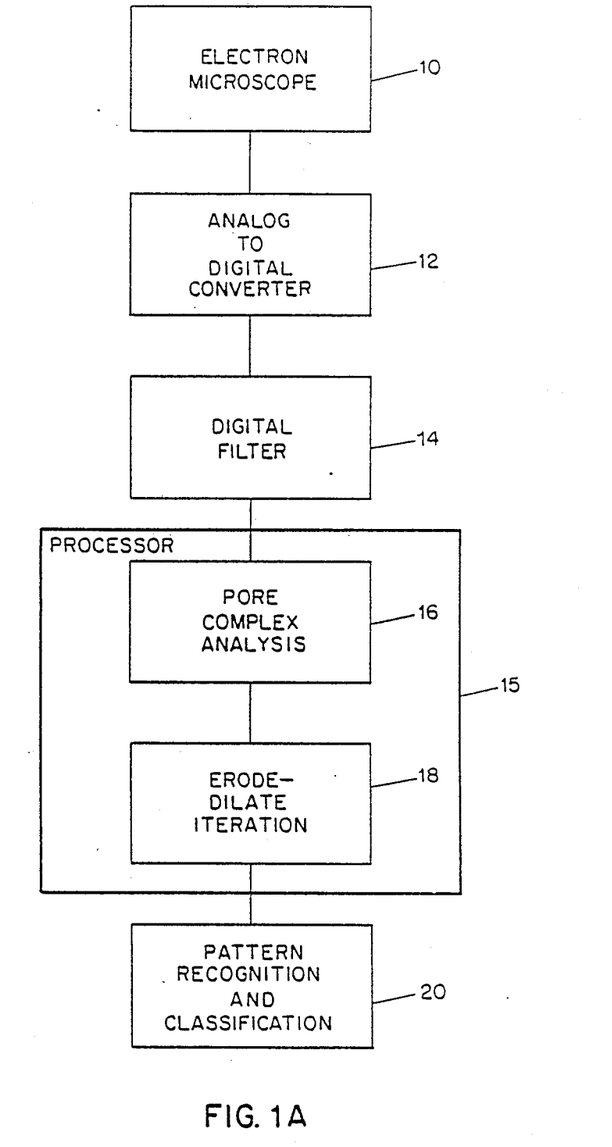
FIG. 1A is a schematic block diagram illustrating the system for analyzing reservoir pore complexes in accordance with the invention and FIG. 1B is a flow chart of the operation of the system shown in FIG. 1A.
Figure 1B:
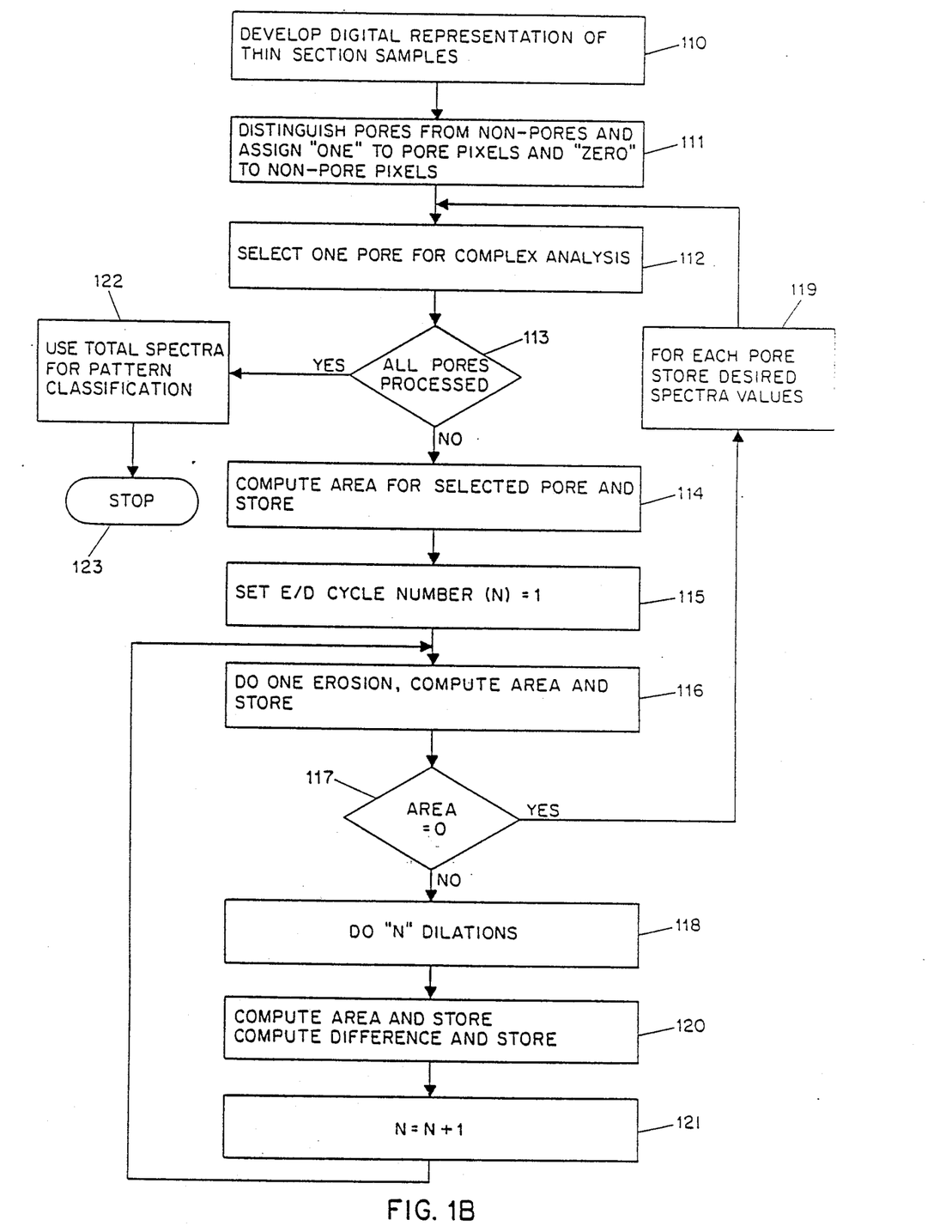
Figure 2:
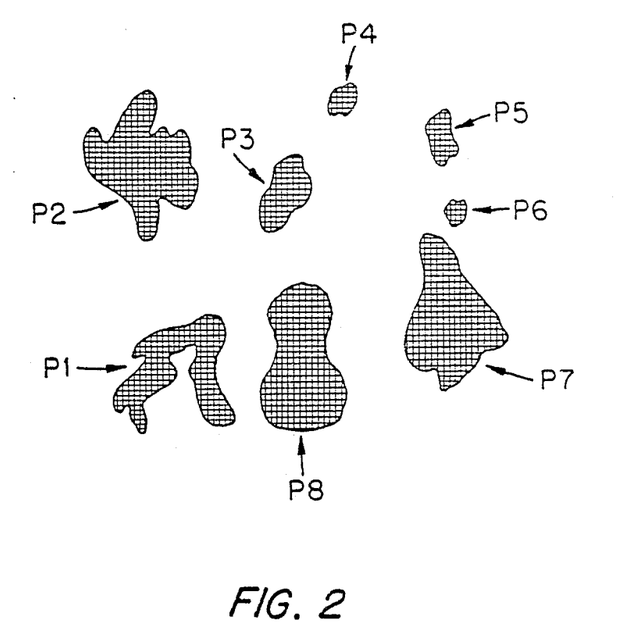
FIG. 2 illustrates the segmentation and labeling of pores in a binary image.

As shown in FIG. 1B, there are developed digital representations of the thin section samples of the rock, represented by block 110 and there is assigned a "one" to the black pore pixels as indicated by block 111.

After each pore has been assigned a unique identification number as shown in FIG. 2, single pores are selected in turn for analysis, as indicated by block 112 until all pores have been analyzed as indicated by block 113.

For each selected pore, there is first computed the pore area and this information is stored, as indicated by block 114.

There is then performed an erosion-dilation cycle of N iterations, beginning with N equal to one, as indicated by block 115. After each erosion there is computed the area and this is stored as indicated by block 116. As long as the erosion has not completely eroded the area, there are preformed N dilations, as indicated by blocks 117 and 118. When the area has been completely eroded, there is stored for that pore the desired spectra information, as indicated by block 119.

After each dilation step there is also computed and stored the resulting area and there is also computed and stored the difference effected by the dilation, as indicated by block 120. Moreover after each dilation, the number N is advanced by one as indicated by block 121, and the process is repeated as represented by the feedback block 116.

After all the pores have been processed, all of the data stored is process and classified as represented by block 122 to derive the complex pore spectra, and then the analysis is complete, as indicated by stop 123.

Figure 7:
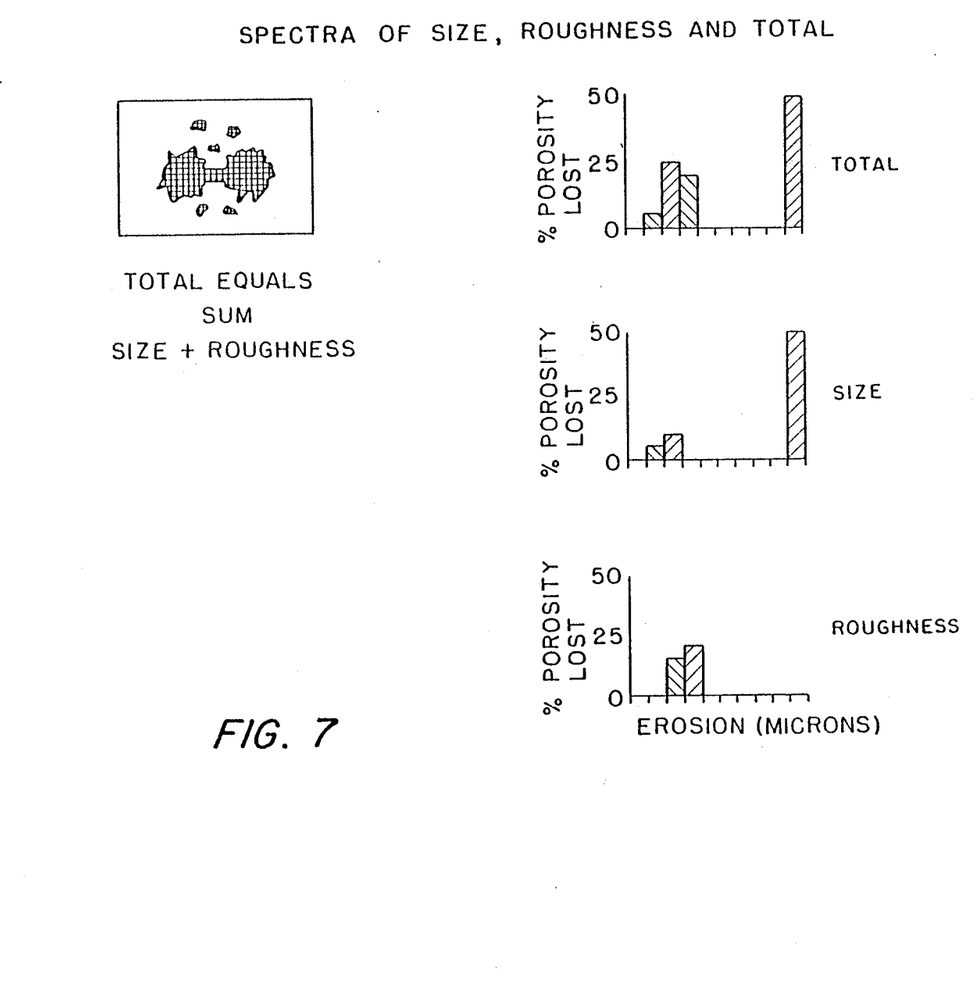
FIG. 7 illustrates a spectrum of information relating to size, roughness and total.
Figure 8:
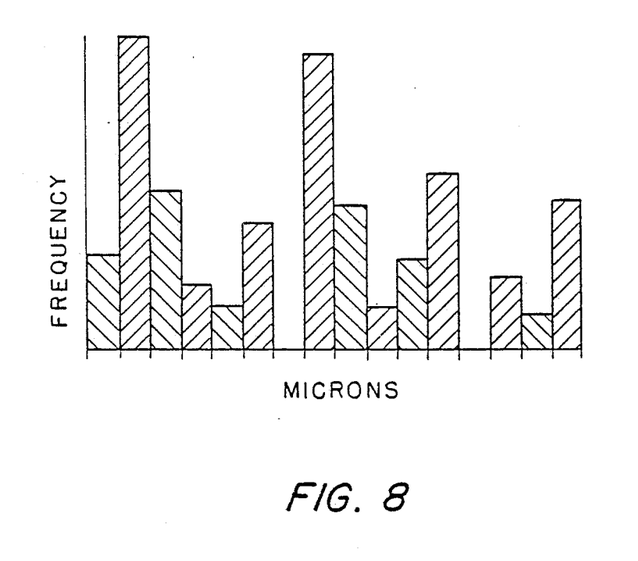
FIG. 8 illustrates a pore throat and a pore throat frequency distribution.
Figure 9:
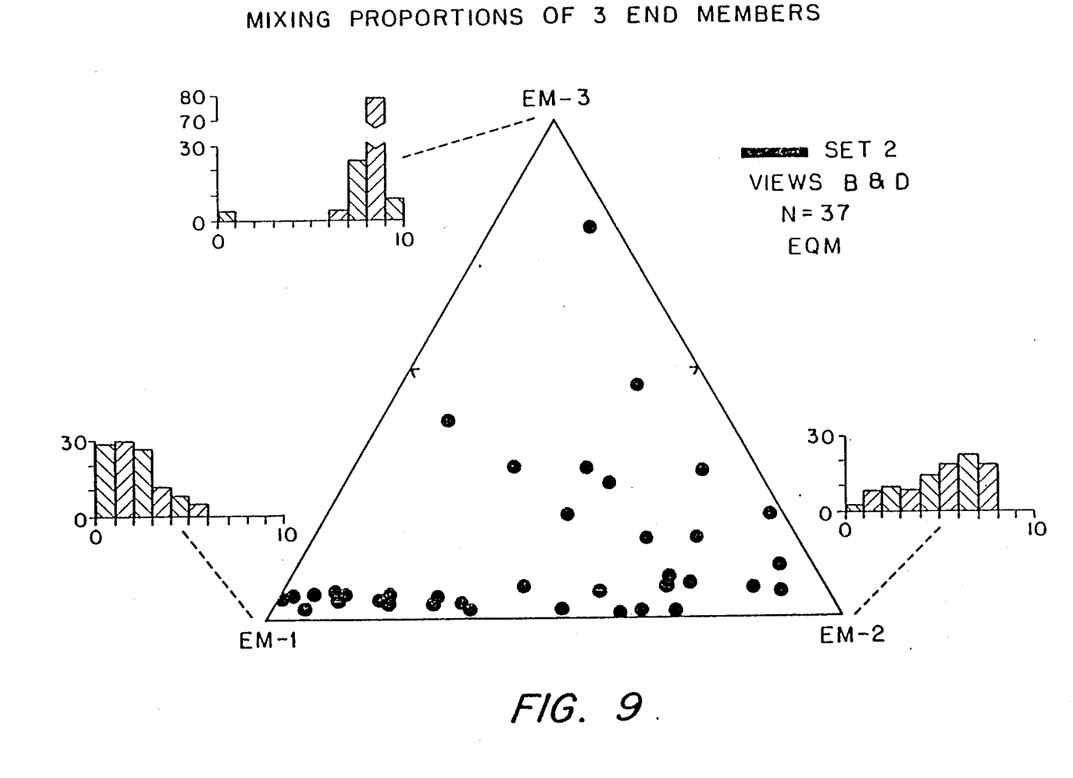
FIG. 9 illustrates the mixing proportions of three end members.

Typical complex pore spectra are shown in FIGS. 7, 8 and 9 and will be discussed further hereinafter. The first operations include estimates of total porosity which is the proportion of blue pixels of unit binary value and, most importantly, total pore perimeter. As explained in *Geometrical Probability* by Kendall and Moran, Hetner Publishing Co., 1963, for thin sections, total pore perimeter is directly proportional to surface area per unit volume as long as the pixel array represents the same total image area. Total pore perimeter is one of the few operations that can be directly related to measured permeability. Other operations exist, such as "unsupervised learning" routines which can erect classification schemes and special programs such as corner detectors which measure asperities. These and other operators have the advantage of being very fast, e.g., a few seconds or less of mini-computer time.

However, more than one sort of pore network can generate similar results from simple operations. Complex operators actually measure the nuances of pore geometry and, as will be shown below, generate pore geometry spectra. Such spectra represent a diagnostic finger print such that it is very unlikely—but not impossible—that two significantly different complexes will yield identical spectra.

The concept of image erosion is a well known one in image processing where it is used both as a smoothing technique and a shape classifier. The concept of erosion has been described, as early as 1968, as use of a "prairie fire" in order to shrink an object to a skeleton or a point. This technique tended to smooth and simplify the object as the "fire" burned in evenly from all sides toward the center. Dilation is described as an operation which will expand (as the "fire" burns out from the center) from the skeleton to be a simplified version of the original object after a number of expansions. For an object such as a pore, one may convert the one binary value to the zero binary value of the outermost layer of pixels of the one binary value in a manner analagous to peeling an onion. This conversion is termed erosion. Repeated erosion, layer by layer, progressively simplifies the object. In the case of pore complexes, progressive erosion, layer by layer, first eliminates or converts the pixels corresponding to micropores as well as small-scale roughness on the pore walls. As cycle after cycle of erosion proceeds, pore throats of greater widths are severed and the surviving elements of the pore complex appear as isolated regions of relatively simple geometry.

Figure 3:
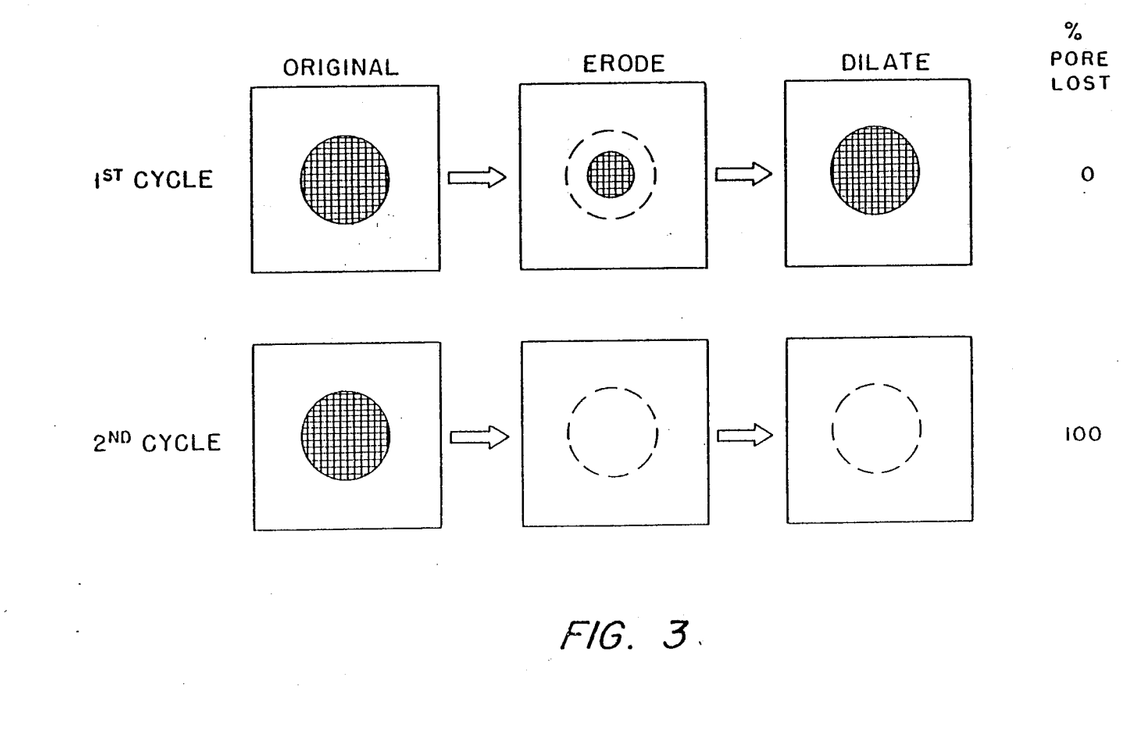
FIG. 3 illustrates an erosion-dilation cycle.
Figure 4:
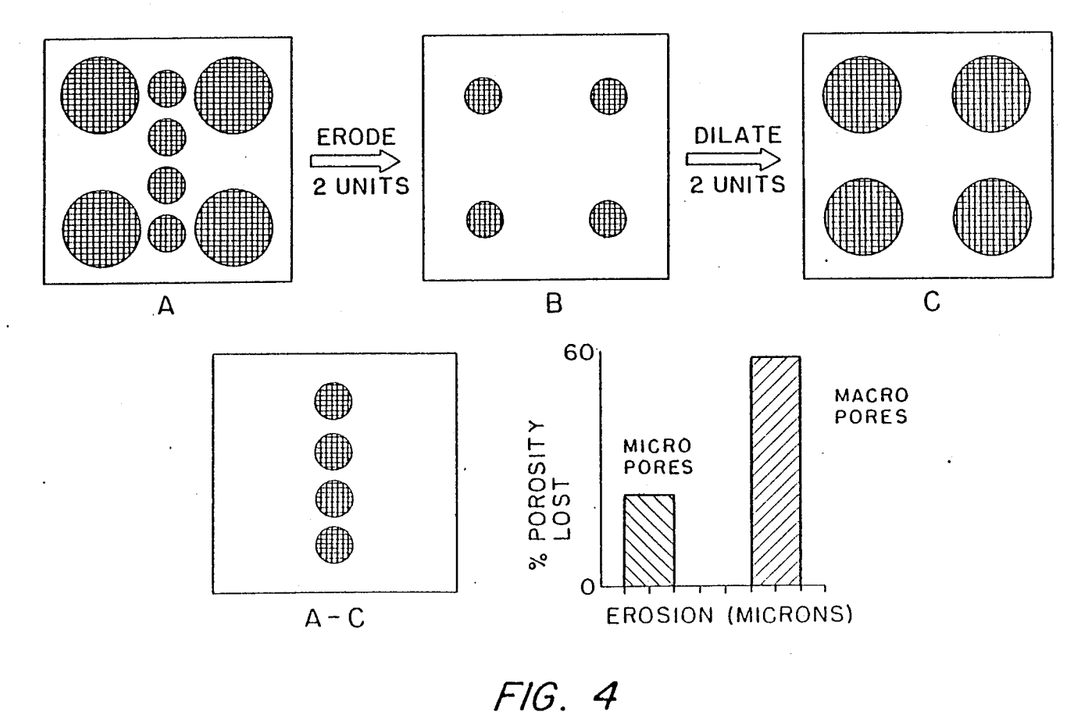
FIG. 4 illustrates the product of an erosion-dilation cycle for an illustrative pore size distribution.
Figure 5:
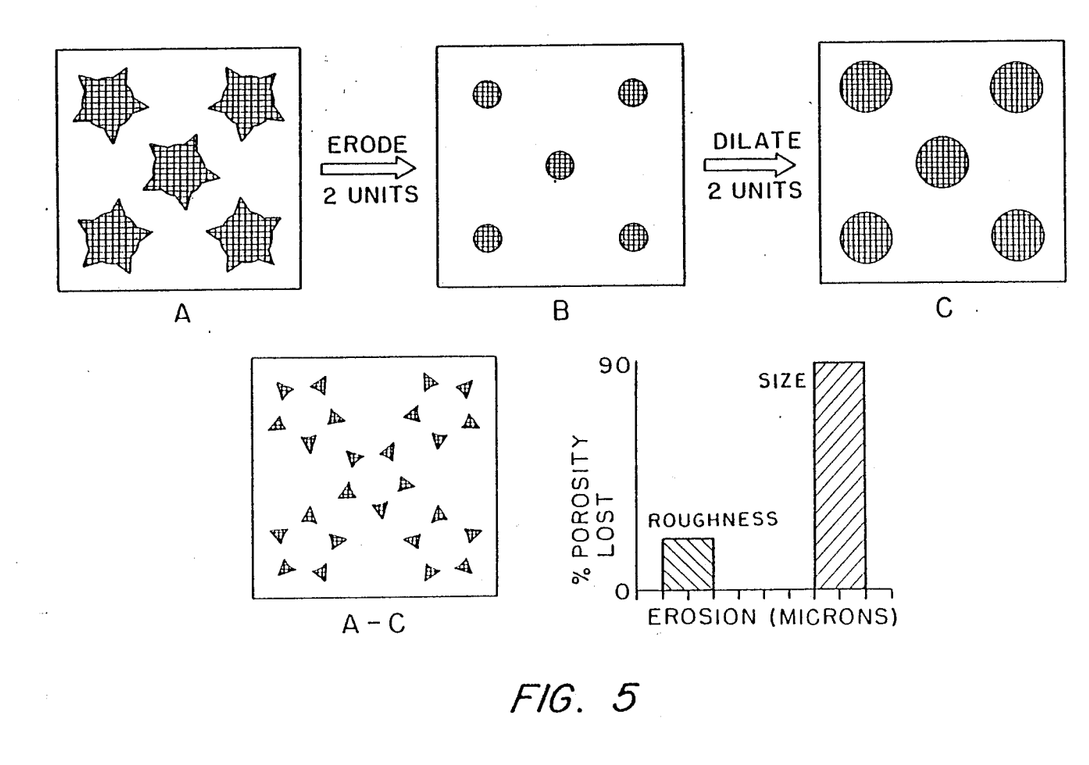
FIG. 5 illustrates the product of an erosion-dilation cycle for an illustrative pore roughness.

Dilation is the reverse of erosion. A layer (or layers) of pixels of unit binary value is added to the object. Dilation after erosion only occurs if "seed" pixels of unit binary value remain. As explained in the article by Young, et al. entitled "A New Implementation for the Binary and Minkowski Operators," *Comp. Graph and Image Proc.*, pp. 189–210 (1981) and as shown in FIG. 3, any objects completely destroyed by erosion cannot undergo dilation. Therefore, size information is carried by the difference between the number of pore-pixels (unit binary value) in the original image and an image in which the areas of pore-pixels have suffered a certain degree of erosion and dilation (FIG. 4). Dilation after erosion need not restore the object to its original shape because irregularities lost via erosion cannot be replaced by dilation (FIG. 5).

The erosion-dilation cycle is a process carried out at block 18 of FIG. 1 by which an erosion or conversion of one layer of pore pixels on the surface takes place and then, if a "seed" pore pixel(s) remains after the erosion is completed, one layer of pore pixels is added by converting a layer of non-pore pixels. The second erosion-dilation cycle will perform two successive erosions of the original object followed by two dilations if a "seed" pixel(s) remains. Successive iterations of the erosion-dilation cycle continue until the last erosion converts or destroys the "seed" pore pixel(s). The pore analysis process classifies pore pixels converted after erosion into a category consisting of those removed from a still existing core (or seed) and those whose conversion results in the total conversion of the pixels of a pore.

Figure 6:
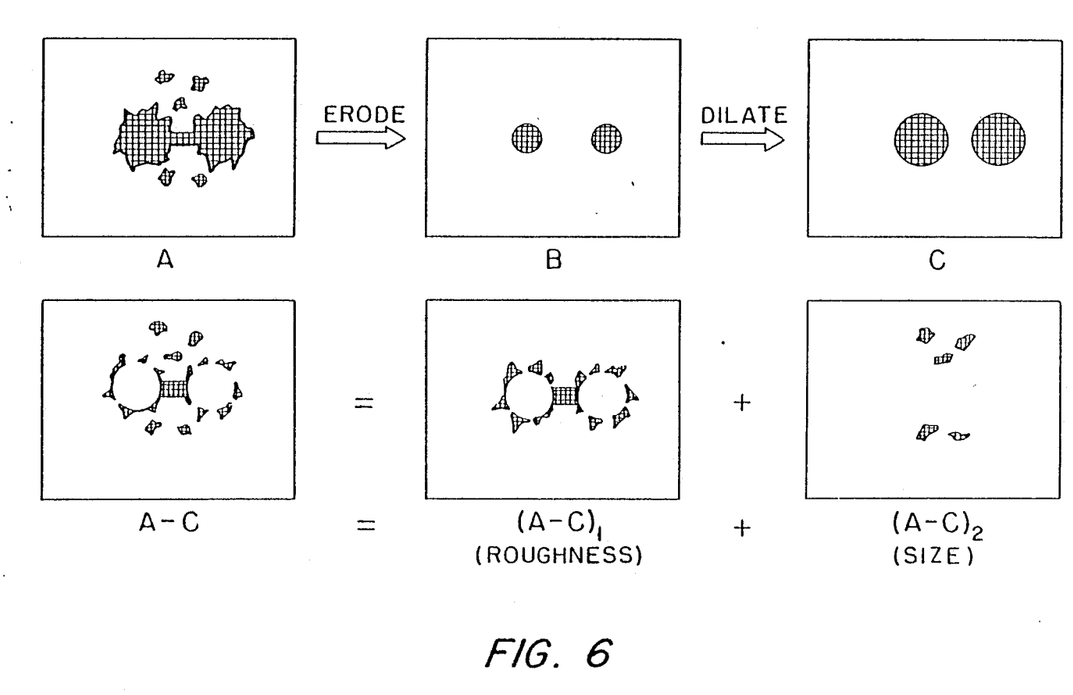
FIG. 6 illustrates an erosion-dilation cycle involving a scene that is a composite of size and roughness.

The algorithm thus produces the amount of pore pixels lost due to roughness and size as erosion-dilation cycles of progressively greater magnitude operates on the original image (FIG. 6). The number of pore pixels lost with each degree of erosion (1 pixel, 2 pixels, etc.) constitutes a pore spectrum. Each field of view thus produces a spectrum for pore size and another for pore roughness (FIG. 7).

Examination of the result of successive iterations of the erosion-dilation cycle (FIG. 8) shows the number of iterations necessary to break (and therefore define) the thinnest pore throat(s), if any. Each iteration will break larger and larger pore throats until finally the basic pore (the areas of largest diameter) remains. This technique may be viewed as the reverse of a mercury injection technique where largest areas of the pore are filled.

The applicants have discovered that, in order to obtain the best results in determining the amount of pore lost during each iteration of the erosion-dilation cycle, the original image is subjected to the N cycles of erosion-dilation and then the difference between the number of pore pixels lost after the $N^{th}$ cycle and the number of pore pixels lost after the previous N-1 cycles is calculated.

For the purposes of this invention, all pore boundaries are classified as interior (completely surrounded by pore) or exterior. At this time, erosion or dilation occurs only from exterior surfaces. Also, the assumption is made that any pore that crosses the scene boundary extends to infinity. Therefore, the boundary of the scene is not subject to erosion or dilation, only the true exterior pore boundaries are so processed.

With the pore complex now delineated by the segmentation procedure, pore geometry is examined in a pattern recognition and classification block 20 (FIG. 1). If pores are either simple two-dimensionally compact objects, e.g. circles, ellipses, triangles, or are even interconnected networks of uniform width, standard measures of size, shape or network properties would serve to characterize the pore complex. Such measurements then would by definition evaluate essential features needed for correct classification or evaluation of the pore system. Accordingly, in image analysis terminology, use of a measurement or set of measurements, which characterizes or classifies the segmented image, is termed feature extraction.

Identification of the correct features is a most critical step in image analysis. If the features are not information-rich with respect to the specific problem being addressed, subsequent analysis of the data carried by the feature will be ineffectual. Conventionally, it is usually not self-evident which measurement of an almost infinite variety will be most useful. Successful feature definition is often a matter of trial-and-error.

One way to minimize the risk of choosing the wrong set of features is to use a measure which in some manner completely describes the system. An example of such a measure in the study of particle shape is a finite Fourier series in polar form. A set for Fourier coefficients which, when graphed, converges to the empiric shape contains all the two-dimensional information present. This sort of variable allows postponement of a choice of features that numerical/statistical methods can be used a posteriori to define the most information-rich portions of the series.

However, a variable similar to a Fourier series is necessary to evaluate pore complexes quantitatively, because it is not known at this time which features correlate best with nuances of flow, log responses or seismic properties. Simple measurements such as diameter, width, length, are not necessarily sufficient in that the discrete parts of the pores viewed in thin section can form extended objects consisting of wider areas or pores connected in complex ways by narrower areas or pore throats. Pore throats in one part of the field of view may be larger than pores in another part. When intergranular porosity is present, the pores may largely follow the grain boundary network. In such cases, where tendrils of pores connect irregularly shaped "blobs" of pores, measures related to simple geometric concepts are difficult to define.

In accordance with our invention, the erosion/dilation concept is used for pore complex analysis. Pore complex analysis requires the use of a data/analytical procedure to evaluate and classify large data sets consisting of pore complexes from many thin sections, each with many fields of view. The optimal situation is that after the erosion-dilation cycle the data be in a form which can be most efficiently and unambiguously analyzed by the analytical algorithm. In that light, the erosion-dilation process of this invention is one which will produce data in the exact form required for analysis by the QMODEL family of pattern recognition/classification algorithms. See, Full, et al., "FUZZY QMODEL—A New Approach for Linear Unmixing," *Math. Geol.*, Vol. 13, n. 4, pp. 331–344.

The measure of pore-complex scale and geometry described below takes advantage of the fact that a given amount of erosion followed by the same amount of dilation need not restore the image to its original state. Small pores may be lost completely during erosion leaving no "seed" pixels for subsequent dilation (FIGS. 3, 4, 6). Similarly, roughness elements lost under the action of erosion will not be restored by subsequent dilation because the dilation process has no "memory" of their existence (FIGS. 5, 6, 7).

The pore complex measure consists of monitoring the proportion of porosity "lost" under progressively more severe cycles of erosion and dilation. Each cycle measures the conversion or loss after erosion and dilation involving a single layer of pore pixels, the second two layers, the third three layers, etc. At some point erosion overwhelms the entire pore complex and the subsequent dilation thus has no seed for use in restoring. The result of the complete process is a frequency distribution of the proportions of total image porosity converted or lost at each cycle—the total equal to 100% (FIG. 7). These distributions will hereafter be termed "pore-complex spectra."

Since the loss due to any particular erosion-dilation cycle can constitute the conversion or loss of an entire pore or the conversion or loss of an angular corner or pore throat, the algorithm of the invention checks to see whether the loss of pixels is due to the loss of an entire pore or to the loss of a portion of a pore, e.g. pore roughness (FIG. 5). Thus, for each field of view three spectra are produced: (1) the total amount of pore image converted or lost per erosion-dilation cycle, (2) pore size lost per erosion-dilation cycle, and (3) pore roughness lost per erosion-dilation cycle. Each erosion-dilation cycle is therefore related to an absolute spatial scale defined by microscope magnification and the size of the pixel grid. The spectra can therefore be scaled in terms of a linear scale such as microns (FIG. 7). Any given pore is thus partitioned into two parts, roughness and size, in a manner slightly analogous to ascribing a single shape to sphericity and roundness.

The relative proportions of the smooth and rough components of porosity (determined by erosion-dilation cycles) are variables important in assessing reservoir quality. The size distribution of each of these components (the erosion-dilation spectra) is also of use in this regard. These variables (smooth proportion, roughness proportion and class-interval proportions of the erosion-dilation spectra) can be used directly to estimate reservoir parameters such as permeability, initial water saturation and residual oil saturation. The erosion-dilation spectra can also be used in objective classification of reservoir pore complexes. That is, the number of kinds of pores (in terms of size and geometry) and their relative proportions can be determined if the erosion-dilation spectra are used as input data for classification algorithms.

The pore complex within a given rock volume represents the time-integrated interaction between the initial properties of a sedimentary deposit and post-depositional, chemical and physical processes. Pressure, temperature, chemistry of formation waters and intrinsic rock properties usually vary in time and space in such a way to augment or detract from a pre-existing pore complex. When sampled on a broad enough scale, the pore complex can be thought of and so classified as a mixture of sub-complexes. For instance, if a rock volume contained only circular pores then everywhere in that volume could be characterized as mixtures of two and member complexes: one consisting of micropores, the other of large pores. In the case of the circular large and small pores, each end member would be represented by a narrow peak on the pore-size spectrum generated by the erosion-dilation algorithm described above (FIG. 4). However, there is no reason to believe that an end member which represents a two-dimensional slice of the three-dimensional pore network need be unimodal, nor that only two end members suffice. End members can be considered to occupy the vertices of a geometric figure which will enclose all observed samples (FIG. 9). This figure, termed a polytope, relates all samples as mixtures of end members. A triangle diagram familiar to all geologists is an example of a three end member polytope. If more than four end members are needed, polytopes have dimensions greater than three.

Thin sections containing end member pore complexes may not be represented in a sample set. Pore complex end members represent extreme conditions in a rock body. They may not be encountered during sampling because such conditions may have affected only a small portion of the rock volume and so be missed in sampling. Indeed, petrogenetic conditions may not have persisted long enough, or were not intense enough, to drive the pore complex into an end member condition. In that case an end member with an associated erosion-dilation spectrum necessary to classify the pore complex in terms of end member proportions which could not have been captured during sampling and would have to be deduced from the pattern of variability of the observed erosion-dilation spectra.

Algorithms which analyze a collection of spectra into end members erect a polytope and calculate end member proportions for each field of view are termed unmixing algorithms. Those algorithms have as their basis the vector analysis algorithm CABFAC, sometimes termed a Q-MODE factor analysis algorithm. The algorithm EXTENDED CABFAC developed by Klovan and Meisch ("EXTENDED CABFAC and QMODEL computer programs for Q-mode factor analysis of compositional data: *Comput. Geosci.,* VI, pp. 161–178) for determining the number of end members in a constant sum system where each pore complex spectrum is viewed as a multidimensional vector may also be used in the present invention.

In classifying pore complex spectra, the unmixing algorithms perform three functions: (1) determine the number of end members, (2) identify the pore complex spectra of end members, and (3) determine mixing proportions of each end member for each observed pore complex spectrum.

The first two functions can be thought of as a pore classification system objectively derived from the reservoir complex. It is linked to pre-existing classifications but carries implicitly within the concept of relative proportion. A pore complex end member might not be unimodal. For instance, if circular macropores and micropores occurred in the same ratio from all thin sections, then that pore combination would be defined analytically as a single end member. Thus, the unmixing algorithms can provide a means of determing the degree of independence of pore varieties observed in thin sections.

The mixing proportions of end member spectra can be used as mappable variables. Changes in pore geometry can be contoured and trends determined. Such maps may prove to be of value in modeling the integrated response of a rock body to flow. In addition, extrapolation of gradients might be useful in either a development or exploration context.

Some elements of pore roughness impede fluid flow because the presence of sharp corners produces points of high surface energy. At these points the water film wetting the pore may thin and even break, allowing petroleum to adhere directly to a portion of the wall, thus producing the deleterious condition of mixed wettability.

Pore throats are another component ascribed to pore roughness by our algorithm. Pore throats, as viewed in thin sections, pertain to any constriction in a pore. The concept is a loose one: a pore throat in one portion of a thin section may be larger than a pore in another. A thin section size frequency distribution of pore throats can be obtained by recording the number of erosion-dilation cycles necessary for a given pore to separate into two pores.

A varible considered of value to many reservoir scientists is surface area of pore per unit volume. This can be obtained using geometric probabilistic results. For a first approximation, one may choose counts of intersections of pore along rows of pixels. As discussed previously, by comparing counts from differently oriented parallel arrays one may also develop an index of pore orientation.

I claim:

1. A process for analyzing reservoir rock complexes comprising the steps of developing a digital representation of at least one scene of a field of view of a rock sample, arranging the digital representation into an array of pixels, separating the pixels representative of the pores and pore throats formed in the rock sample from the pixels representative of the non-porous areas of the rock sample for forming pixel representations of the pore and pore throat areas, progressively eroding and dilating the pore and pore throat representations such that each representation is subject to a reduction of an increasingly larger amount in size followed by a restoration in size until, a result of the last erosion, the representation is eliminated in its entirety, and displaying erosion-dilation spectra relating to the total amount of pore image, the number of pores and the pore roughness lost during each cycle of eroding and dilating.

2. A process according to claim 1 wherein the amount of pore lost during each iteration of the eroding and dilating cycle is determined by subjecting the original image to N cycles of eroding and dilating and then calculating the difference between the amount of pore lost after the $N^{th}$ cycle and the amount of pore lost after $N^{-1}$ cycles of eroding and dilating where N is a plural number and is the number of erosions necessary to eliminate representations of the pore and pore throat areas in their entireties.

3. A process according to claim 1 comprising the further step of generating a pore throat frequency distribution spectrum representative of the number of pore throats severed during each cycle of eroding and dilating.

4. A process according to claim 2 comprising the further step of analyzing the spectra relating to the total amount of pore image, the number of pores and the pore roughness into one or more end members to thereby classify such spectra.

5. A process according to claim 4 further comprising the steps of producing spectra corresponding to multiple fields of view of the same scene of a rock sample and relating to the total amount of pore image, the number of pores and the pore roughness lost during each cycle of eroding and dilating, analyzing said spectra into end members, identifying the pore-complex spectra of said end members and determining the mixing proportions of each end member for each field of view.

6. A process according to claim 4 wherein the step of developing a digital representation of the at least one scene of a field of view of the rock sample comprises the steps of scanning the rock sample to develop an analog signal representative of the brightness of the rock sample, and digitizing said analog signal by incrementally sampling the analog signal.

7. A process according to claim 6 wherein each field of view of the rock sample is viewed through red, blue and green filters to develop color analog signals representative of the intensity of the red, blue and green colors in the rock sample.

8. A process according to claim 7 comprising the initial step of impregnating the porous areas of the rock sample with blue-dyed epoxy and the further step of filtering the digital signals representative of the intensity of the red, blue and green colors in the rock sample to separate the signals representative of the epoxy impregnated pores and pore throats from the non-porous areas of the rock sample.

9. A process according to claim 4 comprising the further step of defining and tabulating the pixels representative of the pores and pore throats formed in the rock sample.

10. A process according to claim 9 comprising the further steps of comparing the pixels representative of the pores and pore throats against the pixels representative of the non-porous areas in the rock sample to develop an indication of the total porosity of the rock sample, measuring the perimeters of the pore and pore throat representative pixels, and adding the measured perimeters to provide an indication of total pore perimeter.

11. A process for analyzing complexes for porosity comprising the steps of developing a digital representation of at least one scene of a field of view of a sample of the complex in the form of a grid of the scene in which each pixel of the scene corresponding to a porous region of the sample is assigned one binary digital value and each pixel of the scene corresponding to a non-porous region is assigned the other binary digital value so that the porous regions correspond in the grid to areas of pixels of the one binary digital value, eroding for each area of pixels of the one binary digital value the size of the area by converting the outer layer of pixels of such area to pixels of the other binary digital value while storing the value of the number of pixels converted, dilating for each area of pixels of the one binary digital value the size of the area by converting to the one binary value the layer of pixels of the other binary value proximate the remaining area of pixels of the one binary value, repeating the eroding and dilating steps for each area of pixels of the one binary digital value and with each repetition increasing the number of eroding steps to convert to the other binary value an additional outer layer of the pixels of the one binary value and similarly increasing thereafter the number of dilating steps, while storing the value of the number of pixels converted by each eroding and dilating operation, such repetition continuing until the number of eroding steps is sufficient to erode all the pixels of the one binary value for each area of the grid of interest, while continuing to store the number of pixels converted by each eroding step and the number of pixels converted by each set of repetitive eroding and dilating steps, and utilizing thereafter the values of the number of pixels converted for each of the eroding steps for deriving pore complex spectra for utilization.

12. The process of claim 11 in which data as to the numbers of pixels converted at each of the eroding steps is utilized to form pore complex spectra relating to the total amount of pore image, the number of pores and the pore roughness.

13. The process of claim 11 in which each field of view of the image scene is viewed through filters of different colors to develop signals representative of different colors for developing different digital representations of the image scene for analysis.

14. A process according to claim 11 wherein the amount of pore converted during each iteration of the eroding and dilating cycle is determined by subjecting the original image to N cycles of eroding and dilating and then calculating the amount of pore lost after the Nth cycle and the amount of pore converted after the Nth and the amount of pore converted after N-1 cycles of eroding and dilating, where N is a plural number and is the number of erosions necessary to eliminate the pixels of the one binary digital value in their entireties.

* * * * *

UNITED STATES PATENT AND TRADEMARK OFFICE
CERTIFICATE OF CORRECTION

PATENT NO. : 4,783,751

DATED : November 8, 1988

INVENTOR(S) : Ehrlich et al.

Page 1 of 2

It is certified that error appears in the above-identified patent and that said Letters Patent is hereby corrected as shown below:

First page, 2nd col., 13th line, "Brunbaugh" should read --Brumbaugh--;

First page, 8th line of ABSTRACT, after "is" insert --then--;

First page, 16th line of ABSTRACT, "numbewr" should read --number--

First page, 45th-from-bottom line of ABSTRACT, "devleoped" should read --developed--;

Col. 2, line 40, "piror" should read --prior--;

Col. 5, line 44, "process" should be --processed--;

Col. 9, line 48, delete "and";

Col. 9, line 54, "Those" should read --These--;

Col. 10, line 12, "determing" should be --determining--;

Col. 10, line 59, after "until," insert --as--;

Col. 11, line 11, "claim 2" should read --claim 3--;

UNITED STATES PATENT AND TRADEMARK OFFICE
CERTIFICATE OF CORRECTION

PATENT NO. : 4,783,751

DATED : November 8, 1988

INVENTOR(S) : Ehrlich et al.

It is certified that error appears in the above-identified patent and that said Letters Patent is hereby corrected as shown below:

Col. 12, line 55, after "Nth" insert -- cycle --.

Signed and Sealed this

Sixteenth Day of January, 1990

Attest:

JEFFREY M. SAMUELS

Attesting Officer     Acting Commissioner of Patents and Trademarks